United States Patent
Bush

(10) Patent No.: US 10,933,156 B2
(45) Date of Patent: *Mar. 2, 2021

(54) SYSTEM AND METHOD FOR DISPENSING MATERIAL

(71) Applicant: The Procter & Gamble Company, Cincinnati, OH (US)

(72) Inventor: Stephan Gary Bush, Liberty Township, OH (US)

(73) Assignee: The Procter & Gamble Company, Cincinnati, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 16/902,407

(22) Filed: Jun. 16, 2020

(65) Prior Publication Data

US 2020/0306407 A1  Oct. 1, 2020

Related U.S. Application Data

(63) Continuation of application No. 16/262,965, filed on Jan. 31, 2019, now Pat. No. 10,716,873.

(60) Provisional application No. 62/624,849, filed on Feb. 1, 2018.

(51) Int. Cl.
| | |
|---|---|
| *A61L 9/14* | (2006.01) |
| *B41J 2/045* | (2006.01) |
| *A45D 34/00* | (2006.01) |
| *B41J 2/38* | (2006.01) |
| *B41J 2/175* | (2006.01) |
| *A45D 40/00* | (2006.01) |
| *B41J 2/18* | (2006.01) |

(52) U.S. Cl.
CPC .............. *A61L 9/14* (2013.01); *A45D 34/00* (2013.01); *A45D 40/00* (2013.01); *B41J 2/0458* (2013.01); *B41J 2/04528* (2013.01); *B41J 2/175* (2013.01); *B41J 2/18* (2013.01); *B41J 2/38* (2013.01); *A61L 2209/11* (2013.01); *A61L 2209/132* (2013.01)

(58) Field of Classification Search
CPC .. A61L 9/14; A61L 2209/11; A61L 2209/132; A45D 40/00; A45D 34/00; B41J 2/38; B41J 2/18; B41J 2/0458; B41J 2/175; B41J 2/04528

See application file for complete search history.

(56) References Cited

U.S. PATENT DOCUMENTS

| | | |
|---|---|---|
| 4,129,391 A | 12/1978 | Gamacher |
| 4,270,526 A | 6/1981 | Morales |
| 4,782,109 A | 11/1988 | Dulaney |
| 4,813,404 A | 3/1989 | Vallis |
| 5,706,038 A | 1/1998 | Jackson |
| 6,017,110 A | 1/2000 | Jackson |
| 6,290,324 B1 | 9/2001 | Jackson |
| 6,312,124 B1 | 11/2001 | Desormeaux |
| 6,341,831 B1 | 1/2002 | Weber |
| 6,543,893 B2 | 4/2003 | Desormeaux |
| 6,622,733 B2 | 9/2003 | Saksa |
| 6,723,077 B2 | 4/2004 | Pickup |
| 6,810,130 B1 | 10/2004 | Aubert |
| 7,500,732 B2 | 3/2009 | James |
| 7,544,190 B2 | 6/2009 | Pickup |
| 7,648,364 B2 | 1/2010 | Dauga |
| 7,798,599 B2 | 9/2010 | Michael |
| 7,824,003 B2 | 11/2010 | Studer |
| 7,890,152 B2 | 2/2011 | Edgar |
| 8,007,062 B2 | 8/2011 | Edgar |
| 8,027,505 B2 | 9/2011 | Edgar |
| 8,231,292 B2 | 7/2012 | Rabe |
| 8,255,089 B2 | 8/2012 | Luc |
| 8,466,213 B2 | 6/2013 | Ueno |
| 8,695,610 B2 | 4/2014 | Samain |
| 8,814,300 B2 | 8/2014 | Shin |
| 8,915,562 B2 | 12/2014 | Edgar |
| 8,942,775 B2 | 1/2015 | Edgar |

(Continued)

FOREIGN PATENT DOCUMENTS

| | | |
|---|---|---|
| CN | 107521229 B | 5/2019 |
| CN | 107639939 B | 2/2020 |

(Continued)

OTHER PUBLICATIONS

Case 15087 Search Report; International Application No. PCT/US2019/015942; 6 pages dated Apr. 16, 2019.
All Office Actions; U.S. Appl. No. 16/262,965.
All Office Actions; U.S. Appl. No. 16/262,967.
All Office Actions; U.S. Appl. No. 16/262,968.
All Office Actions; U.S. Appl. No. 16/262,970.
All Office Actions; U.S. Appl. No. 16/798,559.
All Office Actions; U.S. Appl. No. 16/798,569.
U.S. Appl. No. 17/079,547, filed Oct. 26, 2020, Janette Villalobos Lingoes, et al.
U.S. Appl. No. 17/019,450, filed Sep. 14, 2020, Janette Villalobos Lingoes, et al.
U.S. Appl. No. 16/798,559, filed Feb. 24, 2020, Janette Villalobos Lingoes, et al.

(Continued)

*Primary Examiner* — Geoffrey S Mruk
(74) *Attorney, Agent, or Firm* — Melissa G Krasovec

(57) ABSTRACT

A fluid dispensing method, the method comprising steps of: providing a system comprising a reservoir, a micro-fluidic thermal inkjet print head in fluid communication with the reservoir, a controller and a power source in electrical communication with the controller and the print head, the reservoir containing a fluid, the micro-fluidic thermal inkjet print head comprising nozzles; heating the fluid in the microfluidic device to a temperature of about 40 C to 75 C in less than about 1000 ms; activating the print head to fire the nozzles about 200 fires/nozzle at a first frequency; subsequent to step c, activating the print head to fire the nozzles at a second frequency, the second frequency substantially less than the first frequency; and subsequent to step d, activating the print head to fire the nozzles at a third frequency substantially greater than the first frequency.

11 Claims, No Drawings

(56) References Cited

U.S. PATENT DOCUMENTS

| | | |
|---|---|---|
| 9,020,184 B2 | 4/2015 | Edgar |
| 9,084,587 B2 | 7/2015 | Eckhouse |
| 9,247,802 B2 | 2/2016 | Edgar |
| 9,271,554 B2 | 3/2016 | Nakashima |
| 9,449,382 B2 | 9/2016 | Edgar |
| 9,462,872 B2 | 10/2016 | Edgar |
| 9,522,101 B2 | 12/2016 | Rabe |
| 9,592,666 B2 | 3/2017 | Bush |
| 9,616,447 B2 | 4/2017 | Bush |
| 9,616,668 B1 | 4/2017 | Rabe |
| 9,616,692 B1 | 4/2017 | Rabe |
| 9,650,525 B1 | 5/2017 | Suthar |
| 9,757,947 B2 | 9/2017 | Kuno |
| 9,782,971 B2 | 10/2017 | Vernon |
| 9,814,904 B2 | 11/2017 | Jones |
| 9,878,554 B1 | 1/2018 | Komplin |
| 9,907,734 B2 | 3/2018 | Rabe |
| 9,924,875 B2 | 3/2018 | Rabe |
| 9,925,362 B2 | 3/2018 | Rabe |
| 9,928,591 B2 | 3/2018 | Rabe |
| 9,949,547 B2 | 4/2018 | Rabe |
| 9,949,552 B2 | 4/2018 | Rabe |
| 9,955,769 B2 | 5/2018 | Rabe |
| 9,962,532 B2 | 5/2018 | Rabe |
| 10,016,046 B2 | 7/2018 | Edgar |
| 10,035,355 B2 | 7/2018 | Komplin |
| 10,043,292 B2 | 8/2018 | Edgar |
| 10,092,082 B2 | 10/2018 | Edgar |
| 10,117,500 B2 | 11/2018 | Samain |
| 10,163,230 B2 | 12/2018 | Edgar |
| 10,166,799 B2 | 1/2019 | Rabe |
| 10,188,192 B2 | 1/2019 | Rabe |
| 10,188,193 B2 | 1/2019 | Rabe |
| 10,238,582 B2 | 3/2019 | Rabe |
| 10,265,260 B2 | 4/2019 | Giron |
| 10,314,378 B2 | 6/2019 | Rabe |
| 10,391,042 B2 | 8/2019 | Lingoes |
| 10,449,773 B2 | 10/2019 | Komplin |
| 10,467,779 B2 | 11/2019 | Edgar |
| 10,486,174 B2 | 11/2019 | Edgar |
| 10,511,777 B2 | 12/2019 | Nichols |
| 10,553,006 B2 | 2/2020 | Iglehart |
| 10,576,746 B2 | 3/2020 | Higuchi |
| 10,610,471 B2 | 4/2020 | Lingoes et al. |
| 10,716,873 B2 | 7/2020 | Bush |
| 10,813,857 B2 | 10/2020 | Lingoes |
| 10,849,843 B2 | 12/2020 | Lingoes |
| 2002/0155069 A1 | 10/2002 | Pruche |
| 2003/0060810 A1 | 3/2003 | Syrowicz |
| 2004/0073186 A1 | 4/2004 | Cameron |
| 2004/0186373 A1 | 9/2004 | Dunfield |
| 2004/0223985 A1 | 11/2004 | Dunfield |
| 2004/0246327 A1 | 12/2004 | Elzi |
| 2005/0053628 A1 | 3/2005 | Montanari |
| 2005/0195227 A1 | 9/2005 | Tanaka |
| 2006/0181557 A1 | 8/2006 | Hoisington |
| 2007/0279467 A1 | 12/2007 | Regan |
| 2008/0069620 A1 | 3/2008 | Anderson |
| 2008/0194971 A1 | 8/2008 | Edgar |
| 2010/0002036 A1 | 1/2010 | Jeong |
| 2010/0224209 A1 | 9/2010 | Rabe |
| 2011/0129283 A1 | 6/2011 | Samain |
| 2011/0159463 A1 | 6/2011 | Samain |
| 2011/0229247 A1 | 9/2011 | Song |
| 2013/0158130 A1 | 6/2013 | Heuer |
| 2016/0022972 A1 | 1/2016 | Rabe |
| 2016/0360858 A1 | 12/2016 | Rabe |
| 2017/0157963 A1 | 6/2017 | Rabe |
| 2018/0001646 A1 | 1/2018 | Vernon |
| 2018/0279843 A1 | 10/2018 | Paul |
| 2018/0310693 A1 | 11/2018 | Edgar |
| 2018/0360190 A1 | 12/2018 | Villalobos Lingoes |
| 2018/0360196 A1 | 12/2018 | Meschkat |
| 2018/0360709 A1 | 12/2018 | Rabe |
| 2018/0368727 A1 | 12/2018 | Heath |
| 2019/0080451 A1 | 3/2019 | Iglehart |
| 2019/0193443 A1 | 6/2019 | Wong |
| 2019/0209425 A1 | 7/2019 | Lee |
| 2019/0231661 A1 | 8/2019 | Lingoes |
| 2019/0231662 A1 | 8/2019 | Lingoes |
| 2019/0231671 A1 | 8/2019 | Lingoes |
| 2019/0232649 A1* | 8/2019 | Bush .................... B41J 2/0458 |
| 2019/0263127 A1 | 8/2019 | Tanioku |
| 2020/0188250 A1 | 6/2020 | Lingoes |

FOREIGN PATENT DOCUMENTS

| | | |
|---|---|---|
| DE | 10153249 A1 | 5/2003 |
| DE | 202004003148 U1 | 3/2005 |
| EP | 1010420 A1 | 6/2000 |
| EP | 1236776 A1 | 9/2002 |
| FR | 2933585 B1 | 10/2011 |
| JP | H0465245 U | 6/1992 |
| JP | H04241954 A | 8/1992 |
| JP | H05338141 A | 12/1993 |
| JP | H06278283 A | 10/1994 |
| JP | H09123453 A | 5/1997 |
| JP | 2003052642 A | 2/2003 |
| JP | 2006271654 A | 10/2006 |
| JP | 2006297691 A | 11/2006 |
| KR | 101655978 B1 | 9/2016 |
| WO | 0160925 A3 | 12/2001 |
| WO | 2008010628 A1 | 1/2008 |
| WO | 2008098234 A3 | 11/2008 |
| WO | 2008145258 A1 | 12/2008 |
| WO | 2009036876 A1 | 3/2009 |
| WO | 2009036924 A8 | 7/2009 |
| WO | 2009036925 A8 | 7/2009 |
| WO | 2009157928 A1 | 12/2009 |
| WO | 2010004528 A1 | 1/2010 |
| WO | 2010004531 A1 | 1/2010 |
| WO | 2010027078 A1 | 3/2010 |
| WO | 2010077703 A1 | 7/2010 |
| WO | 2011067761 A1 | 6/2011 |
| WO | 2011079402 A1 | 7/2011 |
| WO | 2012103048 A3 | 10/2012 |
| WO | 2015134020 A1 | 9/2015 |
| WO | 2015134024 A1 | 9/2015 |
| WO | 2015134026 A1 | 9/2015 |
| WO | 2015134027 A1 | 9/2015 |
| WO | 2015134029 A1 | 9/2015 |
| WO | 2017014747 A1 | 1/2017 |
| WO | WO2017014746 A1 | 1/2017 |
| WO | 2017053178 A1 | 3/2017 |
| WO | 2017100150 A1 | 6/2017 |
| WO | 2018088594 A1 | 5/2018 |
| WO | 2018185773 A1 | 10/2018 |

OTHER PUBLICATIONS

U.S. Appl. No. 16/869,586, filed May 7, 2020, Thomas Elliot Rabe, et a.

* cited by examiner

SYSTEM AND METHOD FOR DISPENSING MATERIAL

FIELD OF THE INVENTION

The invention relates to systems and method for dispensing materials. The invention relates particularly to systems and method for dispensing materials by using a thermal jetting system.

BACKGROUND OF THE INVENTION

Dispensing materials via the heating of a volatile carrier to form a transport jet is well known. Thermal ink-jet systems provide a means for the creation and precise deposition of ink droplets upon a substrate. Thermal driven systems may also be used to drive the dispensing or dispersion of other materials, again by volatilizing a carrier or the actual material to be dispensed.

The 'atomization' of fluids to disperse them in an environment for the purpose of depositing the materials upon a substrate is also known. Typical dispersion systems create a set of liquid droplets which are disposed upon a target substrate. Typical fluids are of low viscosity and flow easily within the printing system between the reservoir and the print head nozzles. High viscosity fluids may not flow easily throughout the system and may present a challenge to the successful deposition of such fluids upon a target substrate What is needed is an improved system and method for the deposition of viscous materials upon a target substrate while reducing the degradation of nozzle performance and reducing the operational effect of high viscosity fluids.

SUMMARY OF THE INVENTION

In one aspect, A fluid dispensing method, the method comprising steps of: providing a system comprising a reservoir, a micro-fluidic thermal inkjet print head in fluid communication with the reservoir, a controller and a power source in electrical communication with the controller and the print head, the reservoir containing a fluid, the micro-fluidic thermal inkjet print head comprising nozzles; heating the fluid in the microfluidic device to a temperature of about 40 C to 75 C in less than about 1000 ms; activating the print head to fire the nozzles about 200 fires/nozzle at a first frequency; subsequent to step c, activating the print head to fire the nozzles at a second frequency, the second frequency substantially less than the first frequency; and subsequent to step d, activating the print head to fire the nozzles at a third frequency substantially greater than the first frequency.

DETAILED DESCRIPTION OF THE INVENTION

As used herein, "Particle Size Distribution D50" refers to the diameter where fifty percent of the distribution has a smaller particle size.

In a typical "drop-on-demand" ink jet printing process, a fluid ink is forced under pressure through a very small orifice of a diameter typically about 0.0024 inches (5-50 microns) in the form of minute droplets by rapid pressure impulses. The rapid pressure impulses are typically generated in the print head by either deflection of a piezoelectric crystal vibrating at a high frequency or volatilization of a volatile composition (e.g. solvent, water, propellant) within the ink by rapid heating cycles. The piezoelectric crystal deflection causes the ink to pass through the orifice as minute droplets in proportion to the number of crystal vibrations. Thermal ink jet printers employ heating elements within the print head to volatilize a portion of the composition that propels the vast majority of fluid through the orifice nozzle to form droplets in proportion to the number of on-off cycles for the heating element. The ink is forced out of the nozzle when needed to print a spot on a substrate as part of a desired image. The minute droplets may be energized to achieve an electrical charge and deflected as in the continuous ink jet printing. Conventional inkjet printers are more particularly described in U.S. Pat. Nos. 3,465,350 and 3,465,351.

The present disclosure is directed to a fluid delivery system configured to eject a working fluid from a micro-fluidic die. The die includes one or more activating elements formed in a substrate. The activating elements may be thermal and may utilize electrical resistance heating. Each activating element is disposed adjacent to a fluid chamber and in turn to a nozzle disposed adjacent to the fluid chamber. The micro-fluidic die may further comprise one of more metal traces disposed within the die and in communication with a control element. Well known structures associated with electronic components and the details of semiconductor fabrication have not been included in the description.

In one aspect, the invention comprises an apparatus for dispensing a liquid into an environment or onto a substrate. The apparatus comprises a reservoir containing the liquid. The reservoir is in fluid communication with a dispensing element or print head. The connection between the reservoir and the dispensing element enables the fluid to flow from the reservoir to flow into chambers of the dispensing element. The apparatus further comprises a plurality of nozzles from which fluid is dispensed and a plurality of activation elements associated with the plurality of nozzles. The apparatus also comprises a control element and a power source. The control element determines the timing and distribution of power to the activation elements in order to dispense fluid from the nozzles. As fluid is dispensed, capillary forces draw additional fluid from the reservoir toward the dispensing element chambers and ultimately the nozzles. The apparatus may further comprise one of more metal traces disposed within the die and in communication with a control element. The metal traces may be used to determine the temperature changes of the print head of the apparatus, together with the associated fluid present in the print head, by evaluating the electrical resistance of the metal traces over time.

The determined temperature may be used in the control of the apparatus. In one embodiment, a system comprising a reservoir, a micro-fluidic thermal inkjet print head in fluid communication with the reservoir, a controller and a power source in electrical communication with the controller and the print head, the reservoir containing a fluid, the micro-fluidic thermal inkjet print head comprising nozzles is provided. The system may further comprise heating elements disposed on the micro-fluidic print head, separate from those used as activating elements. The separate heating elements may be commanded by the controller to heat the print head to a predetermined temperature. The temperature of the fluid is tightly coupled to the temperature of the print head due to the small dimensions of the fluid passages and intimate contact between fluid and print head. In one embodiment, the fluid in the microfluidic device is heated to a temperature of about 40 C to about 75 C in less than about 1000 ms. In one embodiment, the fluid may be heated to a temperature of about 65 C in less than about 1000 ms. The heating of the fluid may be useful in reducing the viscosity of the fluid, which may display a reduction in dynamic viscosity with increasing temperature described by, for example, an Arrhenius model. After this heating, the print head nozzles are activated or fired at a first frequency. In one embodiment, the nozzles may be fired for about 200 firings/nozzle. In one embodiment, the first frequency may be between about 200 Hz and about 400 Hz. After this initial firing of the nozzles, the print head nozzles may be fired at a second frequency, wherein the second frequency is substantially less than the first frequency. In one embodiment, the second frequency may be between about 1 Hz and about 10 Hz. In one embodiment, the second frequency may be about 5 Hz. Subsequent to the firing at the second, lower frequency, the nozzles may be fired at a third frequency, wherein the third frequency is substantially greater than the first frequency. In on embodiment, the third frequency may be between about 800 Hz and about 1500 Hz. In one embodiment, the third frequency may be about 1000 Hz.

In one embodiment, the provided fluid may have a dynamic viscosity which is dependent on the shear applied to the fluid. The dynamic viscosity decreases substantially with applied shear, so that firing at the first frequency reduces the dynamic viscosity from the value observed at a resting state. Further, the fluid may exhibit thixotropy, where a certain time is required for the fluid to recover to a higher value of dynamic viscosity, having been subjected to shear. In a preferred embodiment, the second firing frequency is selected to maintain a value of dynamic viscosity below that of the fluid's resting state.

In one embodiment, the apparatus may comprise additional microfluidic channels or other fluid recirculation elements, wherein these additional channels or elements provide fluid flow pathways between the reservoir and the print head chambers prior to dispensing such that the heated fluid may flow and not remain static in the chamber. In one embodiments, the fluid flow may result in shear forces acting upon the fluid which may be useful in reducing the dynamic viscosity of the fluid, making it more amenable to ejection from the micro-fluidic chambers.

In one embodiment, the heating elements may be activated using a modulated voltage having a duty cycle of about 70% and a frequency of about 100 Hz until the temperature of the elements reaches the desired setpoint temperature. As or after the heating elements reach the desired setpoint, the nozzles are fired. In one embodiment, the heating elements may be activated using a full power voltage until the elements reach the desired setpoint temperature. In one embodiment, having substrate heating elements with an electrical resistance of about 21.6 ohms and using an operating voltage of about 11 volts together with an average current of about 350 milliamperes, the elements may be heated from about 25 C to about 65 C is about 500 ms.

In one embodiment, the fluid may comprise a cosmetic ink composition. The cosmetic ink composition can be non-Newtonian, meaning the cosmetic ink composition can have a shear dependent viscosity and/or viscoelastic properties. The cosmetic ink composition can show shear thinning effects under the fluid ejection conditions in which the ink is moved between the cartridge and the print head of an inkjet device. When the cosmetic ink composition is jetted, the shear rate can increase, resulting in a decrease in the viscosity. Thus, the cosmetic ink composition can be stored without particle settling, yet the viscosity and particle size are such that the cosmetic ink composition can still be printed.

The cosmetic ink composition can comprise a particulate material, a (meth)acrylic acid homopolymer or a salt thereof, and a rheology modifier.

In one aspect, the particulate material can be hydrophilic. In one aspect, the particulate material can be substantially coated with one or more ingredients to cause the particulate material to become more hydrophilic. As used herein, "substantially coated" can mean at least about 25%, preferably greater than about 50% surface coverage of the particulate material, more preferably greater than about 75%, most preferably greater than about 90%. Suitable coating ingredients that can render the particulate material hydrophilic in nature can include silica, alumina, polyethylene glycol (PEG) 12 dimethicone, phytic acid, sodium glycerophosphate, and combinations thereof. The particulate material can be substantially coated with one or more coating ingredients using techniques known in the art. One advantage to using a hydrophilic particulate material is that hydrophilic particulate material can be more easily dispersed in water. In one aspect, the particulate material can be titanium and/or iron oxide which has been substantially coated with silica and/or alumina.

Suitable particulate materials can include pigments; encapsulated pigments; mica; clay; mixed metal oxide pigments; metal oxides such as iron oxide, titanium dioxide, zinc oxide, aluminum hydroxide, iron oxide, and combinations thereof; boron nitride; silica; talc; basic lead carbonate; magnesium silicate; baryte ($BaSO_4$); calcium carbonate; pearlescent; colorants, including natural colorants and synthetic monomeric and polymeric colorants; dyes such as azo, indigoid, triphenylmethane, anthraquinone, and xanthine dyes which are designated as D&C and FD&C blues, browns, greens, oranges, reds, yellows, etc.; insoluble metallic salts of certified color additives, referred to as the Lakes; and combinations thereof.

In one aspect, the particulate material can comprise titanium dioxide, iron oxide, and combinations thereof. In one aspect, the titanium dioxide and/or iron oxide can be readily dispersed in water. In one aspect, the titanium dioxide and/or iron oxide is not hydrophobically treated before use in the cosmetic ink composition because it may not be readily dispersed in water. Suitable particulate material can include slurries of titanium dioxide and iron oxide available from KOBO Products Inc (South Plainfield, N.J.), or equivalents.

In one aspect, the cosmetic ink composition comprises a white pigment.

In one aspect, the cosmetic ink composition can have a white appearance. Alternatively, the cosmetic ink composition can have a white appearance with tints of red and/or yellow.

Typical levels of particulate material for sufficient opacity to hide and/or camouflage skin imperfections can be around 30 active wt %. In one aspect, the cosmetic ink composition can comprise greater than about 15 active wt % particulate material, alternatively greater than about 20 active wt %, alternatively greater than about 30 active wt %. In one aspect, the cosmetic ink composition can comprise from about 1 to about 30 active wt % particulate material, alternatively from about 3 to about 25 active wt %, alternatively from about 5 to about 20 active wt %, alternatively from about 8 to about 18 active wt %.

The particulate material can comprise particles having a Particle Size Distribution (PSD) D50 of about 100 nm to about 2,000 nm, alternatively from about 150 nm to about 1,000 nm, alternatively from about 200 nm to about 450 nm, alternatively from about 200 nm to about 350 nm. In one aspect, the particulate material can comprise particles having a PSD D90 of less than about 2 µm, alternatively less than about 1 µm. In one aspect, the particulate material can comprise particles having a PSD D90 of from about 700 to about 900 µm. Without being limited by theory, it is believed that if the particles are too big, they can clog the microfluidic channels of the cartridge and disrupt printing. One skilled in the art would understand that an acceptable particle size can vary depending on print head die architecture. In one aspect, the particulate material can comprise any PSD so long as the particles can move through the microfluidic channels of the cartridge and/or the print head without causing clogging. The Particle Size Distribution can be measured according to the Particle Size Distribution Method described hereafter.

The particulate material can have a refractive index of between about 1.1 and about 5.0, alternatively from about 1.5 to about 4, alternatively from about 2 to about 3.

The particulate material can have a density range of from about 1.5 to about 6 g/mL, alternatively from about 2 to about 4 g/mL.

The cosmetic ink composition can comprise a rheology modifier. Rheology modifiers can assist in preventing settling by keeping the particles uniformly suspended such that little to no agitation of the cosmetic ink composition is needed.

One preferred group of rheology modifiers are ASE polymers. ASE polymers contain a balance of hydrophilic (meth)acrylic acid monomers and hydrophobic (meth)acrylate ester monomers and can be supplied at high volume solids in liquid form. ASE polymers rely on a change from low to high pH (neutralization) to trigger thickening. The "trigger" is built into the polymer by creating an approximately 50:50 ratio of (meth)acrylic acid, which is soluble in water, and a (meth)acrylate ester, which is not soluble in water. When the acid is un-neutralized (low pH), the polymer is insoluble in water and does not thicken. When the acid is fully neutralized (high pH), the polymer becomes soluble and thickens. ASE polymers are supplied at low pH (<5) and maintain a low as-supplied viscosity (<100 cP) at solids of up to 35%. When subject to a pH of about 7 or higher, ASE polymers solubilize, swell, and thicken the composition through volume exclusion. The degree of thickening can be related to the molecular weight of the polymer. Because their performance depends on water absorption and swelling, ASE polymers tend to be very high in molecular weight, which allows them to thicken efficiently. The rheology profiles ASE polymers create are typically steeply shear-thinning (pseudoplastic), and thus ASE polymers are well suited to build high viscosity at very low shear rates. Different rheological characteristics can be achieved by manipulating the molecular weight, as well as the types and amounts of acid and ester monomers, of the polymer.

In one aspect, the hydrophilic monomers of the ASE polymer can include (meth)acrylic acid and maleic acid. In one aspect, the hydrophobic monomers of the ASE polymer can include the esters of (meth)acrylic acid with $C_1$- to $C_4$-alcohols, in particular ethyl acrylate, butyl acrylate, and methyl methacrylate.

In one aspect, the ASE polymer can be synthesized from 10-90 wt % of Hydrophilic Monomer A and 10-90 wt % of Hydrophobic Monomer B. The structure of Hydrophilic Monomer A and Hydrophobic Monomer B are shown below.

Hydrophilic Monomer A

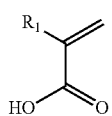

Hydrophobic Monomer B

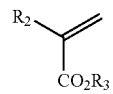

wherein $R_1$ and $R_2$ are independently hydrogen or methyl;
wherein $R_3$ is $C_1$ to $C_4$ alkyl.

Yet another group of rheology modifier suitable for use in the cosmetic ink composition described herein are HASE polymers. These are tertiary polymers that build on the ASE polymer chemistry by adding a hydrophobic acrylic ester and/or vinyl ester monomer to the polymer composition. HASE polymers retain the pH dependent behavior of their ASE counterparts, but in addition to absorbing water, HASE polymers also thicken via hydrophobe association. This mechanism, known as associative thickening (i.e. associating with any hydrophobic moiety in the composition), offers performance properties over a wider range of shear levels and enables a wider range of rheology profiles than is possible with volume exclusion thickeners such as ASE and cellulosic compositions.

The hydrophilic and hydrophobic monomers of the HASE polymers can be the same as described with respect to the ASE polymers. The associative monomer of the HASE polymer can be a monomer that shows a strong hydrophobic character. A preferred associative monomer is ester of (meth)acrylic acid with $C_8$-$C_{22}$ alcohols.

In one aspect, the HASE polymer can be synthesized from 10-90 wt % Hydrophilic Monomer A, 10-90 wt % Hydrophobic Monomer B, and 0.01 to 2 wt % Associative Monomer C. The structure of Associate Monomer C is shown below.

Associative Monomer C

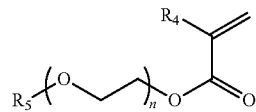

wherein $R_4$ is hydrogen or methyl;
wherein $R_5$ is $C_8$ to $C_{22}$ alkyl;
wherein n is an integer from 0 to 50.

Alternatively, the HASE polymer can be synthesized from 10-90 wt % Hydrophilic Monomer A, 10-90 wt % Hydrophobic Monomer B, and 0.01 to 2 wt % Associative Monomer D. The structure of Associative Monomer D is shown below.

Associative Monomer D

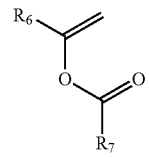

wherein $R_6$ is hydrogen or methyl;
wherein $R_7$ is $C_8$ to $C_{22}$ alkyl.

In one aspect, the associative monomer can be selected from the group consisting of steareth-20 methacrylate, beheneth-25 methacrylate, vinyl neodecanoate, and combinations thereof. In one aspect, more than one associative monomers can be used in the synthesis of the HASE polymer.

In one aspect, ASE and HASE polymers can comprise a cross-linking agent. The cross-linking agent can contain at least two ethylenically unsaturated moieties, alternatively at least three ethylenically unsaturated moieties. Suitable cross-linking agents can include divinyl benzene, tetra allyl ammonium chloride, allyl acrylates, methacrylates, diacrylates, dimethacrylates of glycols and polyglycols, butadiene, 1,7-octadiene, allyl-acrylamides, allyl-methacrylamides, bisacrylamidoacetic acid, N, N'-methylene-bisacrylamide, polyol polyallylethers such as polyallylsaccharose and pentaerythrol triallylether, and mixtures thereof.

In one aspect, the cross-linking agent can be present at a level of from about 25 to about 5,000 ppm, alternatively from about 50 to about 1,000 ppm, alternatively from about 100 to about 500 ppm.

Another group of rheology modifiers are hydrophobically-modified ethylene oxide-based urethane (HEUR) polymers. Unlike ASE or HASE-type rheology modifiers, HEUR polymers are non-ionic and soluble at any pH. This solubility is due to the polymer's ethylene oxide backbone, which is water soluble and makes up the majority of the polymer structure. Thus, HEUR polymers require a hydrophobic moiety in the composition to interact with the ethylene oxide backbone to impart structure. The cosmetic ink composition can comprise a HEUR polymer. Alternatively, the cosmetic ink composition comprises little to no hydrophobic moieties and does not comprise a HEUR polymer.

The rheology modifier can be a (meth)acrylate polymer, a (meth)acrylate copolymer, and mixtures thereof. The rheology modifier can be selected from the group consisting of ASE polymers, HASE polymers, and combinations thereof. Suitable HASE polymers can include ACULYN™ Excel; ACRYSOL™ TT615; ACULYN™ 22; ACULYN™ 88; (all available from The DOW Chemical Company, Lake Zurich, Ill.); and combinations thereof. Suitable ASE polymers can include Rheovis® 1125 (available from BASF Corporation, Charlotte, N.C.), ACULYN™ 33; ACULYN™ 38 (both available from The DOW Chemical Company, Lake Zurich, Ill.); and combinations thereof. The cosmetic ink composition can comprise an ASE polymer. Alternatively, the cosmetic ink composition can comprise an HASE polymer.

The rheology modifier does not consist of a surfactant, an amine oxide, and/or a cellulosic ether.

The cosmetic ink composition can comprise any amount of rheology modifier so long as the first dynamic viscosity of the cosmetic ink composition is greater than about 1,100 cP at a shear rate of 0.1 sec$^{-1}$ measured at 25° C. The cosmetic ink composition can comprise greater than about 0.30 active wt % rheology modifier, alternatively greater than about 0.40 active wt %, alternatively greater than about 0.50 active wt %. The cosmetic ink composition can comprise from about 0.30 to about 1 active wt % rheology modifier, alternatively from about 0.30 to about 0.80 active wt %, alternatively from about 0.40 to about 0.50 active wt %. Active wt % can be measured using standard High Performance Liquid Chromatography-Mass Spectrometry (HPLC-MS) techniques. One advantage to keeping the level of rheology modifier within this range is that the viscosity of the cosmetic ink composition can be built such that the particles can be suspended in the composition. The particles can be suspended for about 11 days or more at 25° C., alternatively about 30 days or more at 25° C., alternatively for about 90 days or more at 25° C., alternatively for about 300 days or more at 25° C. Without being limited by theory, it is believed that at levels of rheology modifier below this range the particles may not be sufficiently suspended and settling may occur. If the level of rheology modifier is too high, the viscosity of the cosmetic ink composition may increase to a point that can impact jetting (i.e. the cosmetic ink composition may not shear thin enough for efficient printing).

In one aspect, the cosmetic ink composition can be substantially free of neutral inorganic salts (as compared to an alkali salt base, like NaOH). Without being limited by theory, it is believed that neutral inorganic salts, such as calcium chloride or sodium chloride, can increase the ionic strength of the cosmetic ink composition and can disrupt the internal structure, thus impacting stability. It is known that HASE and/or ASE polymers become polyelectrolytes at high pHs. As pH increases, the carboxylic acids on the HASE and/or ASE polymers can be neutralized, generating ionic groups on the polymer chains that can produce electrostatic repulsion. These electrostatic repulsions can cause the polymer to expand and form an internal structure in the composition. It is believed that inorganic neutral salts can shield this electrostatic repulsion and can cause the HASE and/or ASE polymer to change structure, and thus its effectiveness in promoting stability.

The cosmetic ink composition can comprise a (meth)acrylic acid homopolymer or a salt thereof. Non-limiting examples of acceptable salts can include sodium, potassium, ammonium, and mixtures thereof. The (meth)acrylic acid homopolymer or salt thereof can be a low molecular weight material that can act to control particle size and can help maintain a low viscosity in the cosmetic ink composition. The (meth)acrylic acid homopolymer or salt thereof does not greatly increase viscosity of the cosmetic ink composition. Non-limiting examples of suitable (meth)acrylic acid homopolymers or salt thereof can include sodium polyacrylate such as Darvan® 811D (available from RT Vanderbilt Holding Company Inc., Norwalk, Conn.), ammonium polyacrylate having a weight average molecular weight of about 3,500 daltons such as Darvan® 821A (available from RT Vanderbilt Holding Company Inc.), and combinations thereof. The (meth)acrylic acid homopolymer or salt thereof have a weight average molecular weight of less than about 20,000 daltons, preferably less than about 10,000 daltons, more preferably less than about 5,000 daltons. The cosmetic ink composition can comprise a (meth)acrylic acid homopolymer or salt thereof having a weight average molecular weight of from about 1,000 to about 20,000 daltons, alternatively from about 1,000 to about 10,000 daltons, alternatively from about 2,000 to about 5,000 daltons, alternatively from about 2,500 to about 4,000 daltons. Weight average molecular weight can be measured by standard High Performance Size-Exclusion Chromatography per ASTM method D5296-11 (Sep. 1, 2011).

In one aspect, the (meth)acrylic acid homopolymer or salt thereof is not a film forming polymer. Without being limited by theory it is believed that the (meth)acrylic acid homopolymer or salt thereof will not form a film because of the low molecular weight.

The cosmetic ink composition can comprise from about 0.01 to about 1 active wt % (meth)acrylic acid homopolymer or salt thereof, alternatively from about 0.10 to about 0.85 active wt %, alternatively from about 0.20 to about 0.75 active wt %, alternatively about 0.30 to about 0.65 active wt %. Without being limited by theory, it is believed that the (meth)acrylic acid homopolymer or salt thereof can control agglomeration, and thus the particle size, of the particulate material by creating a negative surface charge around the particles. Thus, the (meth)acrylic acid homopolymer or salt thereof can help to maintain a particle size that is compatible with printer cartridges and nozzles. Without being limited by theory, it is believed that a cosmetic ink composition comprising below 0.01 active wt % (meth)acrylic acid homopolymer or salt thereof may not have sufficient particle size control and/or the viscoelastic modulus may be too high to allow for reliable refill of the microfluidics.

The ratio of the (meth)acrylic acid homopolymer or salt thereof to the rheology modifier can be less than about 1. The ratio of (meth)acrylic acid homopolymer or salt thereof to rheology modifier can be from about 0.10 to about 0.75, alternatively from about 0.30 to about 0.65. Without being limited by theory it is believed that if the level of (meth) acrylic acid homopolymer or salt thereof is greater than the level of rheology modifier, the rheology modifier may not be able to build the internal structure needed to suspend the particles. If the ratio of (meth)acrylic acid homopolymer or salt thereof to rheology modifier is too low, agglomeration may not be well controlled and the particle size may become too large to fit through printer nozzles, making printing difficult.

It is believed that stability is inversely proportional to the level of (meth)acrylic acid homopolymer or salt thereof and directly proportional to the level of rheology modifier.

In one embodiment, the fluid to be dispensed may comprise a particulate material having a Particle Size Distribution D50 of 100 nm to 2,000 nm; a (meth)acrylic acid homopolymer or salt thereof having a weight average molecular weight of less than 20,000 daltons; and a rheology modifier, wherein the rheology modifier is selected from the group consisting of alkali swellable emulsion polymers, hydrophobically modified alkali swellable emulsion polymers, and combinations thereof. In this embodiment the fluid has a first dynamic viscosity of greater than 1,100 cP at a shear rate of 0.1 sec-1 measured at 25 C and a second dynamic viscosity of less than 100 cP at a shear rate of 1,000 sec-1 measured at 25 C.

The methods of the invention may be utilized together with appropriate apparatus in the deposition of fluids upon substrates for any intended application of the fluids to a substrate, including surface care and the application of a cosmetic fluid to the substrate.

Values disclosed herein as ends of ranges are not to be understood as being strictly limited to the exact numerical values recited. Instead, unless otherwise specified, each numerical range is intended to mean both the recited values and any integers within the range. For example, a range disclosed as "1 to 10" is intended to mean "1, 2, 3, 4, 5, 6, 7, 8, 9, and 10."

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for dispensing fluids, the method comprising steps of:
    a. providing a system comprising a reservoir, a microfluidic thermal inkjet print head in fluid communication with the reservoir, a controller and a power source in electrical communication with the controller and the print head, the reservoir containing a fluid, the microfluidic thermal inkjet print head comprising nozzles;
    b. heating the fluid in the microfluidic device to a temperature of about 40 C to 75 C in less than about 1000 ms;
    c. activating the print head to fire the nozzles at a first frequency; and
    d. subsequent to step c, activating the print head to fire the nozzles at a second frequency, the second frequency substantially less than the first frequency.

2. The method according to claim 1 wherein the first frequency is between about 800 Hz and about 1500 Hz.

3. The method according to claim 1 wherein the second frequency is between about 1 Hz and about 10 Hz.

4. The method according to claim 1 wherein the second frequency is about 5 Hz.

5. The method according to claim 1 wherein the first frequency is about 1000 Hz.

6. The method according to claim 1 wherein the method further comprises the step of activating the nozzles for about 200 activations per nozzle.

7. The method according to claim 6 wherein the step of activating the nozzles for about 200 activations per nozzle is after step b and before step c.

8. The method according to claim 1 wherein the step of heating the fluid comprises heating the fluid to a temperature of about 65 C.

9. The method according to claim 1 wherein the step of providing a micro-fluidic thermal inkjet print head comprises providing a thermal inkjet print head comprising a thermal fluid recirculation element.

10. The method according to claim 1 wherein the step of providing a fluid comprises providing a fluid comprising:
    a. a particulate material having a Particle Size Distribution D50 of 100 nm to 2,000 nm;
    b. a (meth)acrylic acid homopolymer or salt thereof having a weight average molecular weight of less than 20,000 daltons; and
    c. a rheology modifier, wherein the rheology modifier is selected from the group consisting of alkali swellable emulsion polymers, hydrophobically modified alkali swellable emulsion polymers, and combinations thereof;
    wherein the fluid has a first dynamic viscosity of greater than 1,100 cP at a shear rate of 0.1 sec$^{-1}$ measured at 25 C and a second dynamic viscosity of less than 100 cP at a shear rate of 1,000 sec$^{-1}$ measured at 25 C.

11. A method for dispensing fluids, the method comprising steps of:
   a. providing a system comprising a reservoir, a microfluidic thermal inkjet print head in fluid communication with the reservoir, a controller and a power source in electrical communication with the controller and the print head, the reservoir containing a fluid, the microfluidic thermal inkjet print head comprising nozzles, wherein the fluid has a shear dependent viscosity;
   b. heating the fluid in the microfluidic device to a temperature of about 40 C to 75 C in less than about 1000 ms;
   c. activating the print head to fire the nozzles to dispense the fluid at a first dynamic viscosity of greater than 1,100 cP at a shear rate of 0.1 sec$^{-1}$ measured at 25 C; and
   d. activating the print head to fire the nozzles to dispense the fluid at a second dynamic viscosity of less than 100 cP at a shear rate of 1,000 sec$^{-1}$ measured at 25 C.

* * * * *